(12) United States Patent
Sheldon et al.

(10) Patent No.: US 7,502,646 B2
(45) Date of Patent: *Mar. 10, 2009

(54) PACING MODE EVENT CLASSIFICATION WITH RATE SMOOTHING AND INCREASED VENTRICULAR SENSING

(75) Inventors: Todd J. Sheldon, North Oaks, MN (US); Scott R. Stanslaski, Shoreview, MN (US); Michael O. Sweeney, Chestnut Hill, MA (US); Robert A. Betzold, Fridley, MN (US); Douglas A. Hettrick, Blaine, MN (US); Paul A. Belk, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 400 days.

This patent is subject to a terminal disclaimer.

(21) Appl. No.: 11/461,141

(22) Filed: Jul. 31, 2006

(65) Prior Publication Data
US 2008/0027490 A1    Jan. 31, 2008

(51) Int. Cl.
*A61N 1/362* (2006.01)
(52) U.S. Cl. .......................................................... 607/9
(58) Field of Classification Search ..................... 607/9, 607/14
See application file for complete search history.

(56) References Cited

U.S. PATENT DOCUMENTS

| 3,057,356 | A | 10/1962 | Greatbatch |
| 3,253,596 | A | 5/1966 | Keller |
| 3,478,746 | A | 11/1969 | Greatbatch |
| 3,595,242 | A | 7/1971 | Berkovits |
| 3,648,707 | A | 3/1972 | Greatbatch |
| 3,747,604 | A | 7/1973 | Berkovits |
| 4,312,355 | A | 1/1982 | Funke |
| 4,386,610 | A | 6/1983 | Leckrone |
| 4,428,378 | A | 1/1984 | Anderson et al. |
| 4,432,362 | A | 2/1984 | Leckrone et al. |
| 4,476,868 | A | 10/1984 | Thompson |
| 4,523,593 | A | 6/1985 | Rueter et al. |
| 4,577,633 | A | 3/1986 | Berkovits et al. |
| 4,587,970 | A | 5/1986 | Holley et al. |
| 4,726,380 | A | 2/1988 | Vollmann et al. |
| 4,727,877 | A | 3/1988 | Kallok |
| 4,856,523 | A | 8/1989 | Sholder et al. |
| 4,856,524 | A | 8/1989 | Baker |
| 4,880,005 | A | 11/1989 | Pless et al. |
| 4,890,617 | A | 1/1990 | Markowitz et al. |
| 4,932,046 | A | 6/1990 | Katz et al. |
| 4,941,471 | A | 7/1990 | Mehra |
| 4,953,551 | A | 9/1990 | Mehra et al. |
| 5,052,388 | A | 10/1991 | Sivula et al. |
| 5,085,215 | A | 2/1992 | Nappholz et al. |
| 5,097,832 | A | 3/1992 | Buchanan |

(Continued)

FOREIGN PATENT DOCUMENTS

EP    0363015    4/1990

(Continued)

*Primary Examiner*—George R Evanisko
*Assistant Examiner*—Amanda Patton
(74) *Attorney, Agent, or Firm*—Stephen W. Bauer

(57) ABSTRACT

An implantable medical device operates according to a ventricular pacing protocol (VPP) that precludes ventricular pacing in any cardiac cycle where a sensed ventricular event has occurred in the preceding cycle. Improved ventricular sensing, detection and classification is provided.

22 Claims, 13 Drawing Sheets

U.S. PATENT DOCUMENTS

| | | |
|---|---|---|
| 5,117,824 A | 6/1992 | Keimel et al. |
| 5,133,350 A | 7/1992 | Duffin |
| 5,144,950 A | 9/1992 | Stoop et al. |
| 5,163,427 A | 11/1992 | Keimel |
| 5,188,105 A | 2/1993 | Keimel |
| 5,188,117 A | 2/1993 | Steinhaus et al. |
| 5,228,438 A | 7/1993 | Buchanan |
| 5,273,035 A | 12/1993 | Markowitz et al. |
| 5,292,340 A | 3/1994 | Crosby et al. |
| 5,318,594 A | 6/1994 | Limousin et al. |
| 5,334,220 A | 8/1994 | Sholder |
| 5,345,362 A | 9/1994 | Winkler |
| 5,372,607 A | 12/1994 | Stone et al. |
| 5,388,586 A | 2/1995 | Lee et al. |
| 5,417,714 A | 5/1995 | Levine et al. |
| 5,522,859 A | 6/1996 | Stroebel et al. |
| 5,540,725 A | 7/1996 | Bornzin et al. |
| 5,584,868 A | 12/1996 | Salo et al. |
| 5,591,214 A | 1/1997 | Lu |
| 5,626,623 A | 5/1997 | Kieval et al. |
| 5,643,326 A | 7/1997 | Weiner et al. |
| 5,674,257 A | 10/1997 | Stroebel et al. |
| 5,697,958 A | 12/1997 | Paul et al. |
| 5,725,561 A | 3/1998 | Stroebel et al. |
| 5,741,308 A | 4/1998 | Sholder et al. |
| 5,814,077 A | 9/1998 | Sholder et al. |
| 5,836,974 A | 11/1998 | Christini et al. |
| 5,861,007 A | 1/1999 | Hess et al. |
| 5,873,895 A | 2/1999 | Sholder et al. |
| 5,954,755 A | 9/1999 | Casavant |
| 5,999,850 A | 12/1999 | Dawson et al. |
| 6,058,326 A | 5/2000 | Hess et al. |
| 6,122,546 A | 9/2000 | Sholder et al. |
| 6,128,529 A | 10/2000 | Esler et al. |
| 6,128,534 A | 10/2000 | Park et al. |
| 6,141,586 A | 10/2000 | Mower |
| 6,169,918 B1 | 1/2001 | Haefner et al. |
| 6,198,968 B1 | 3/2001 | Prutchi et al. |
| 6,256,541 B1 | 7/2001 | Heil et al. |
| 6,321,115 B1 | 11/2001 | Mouchawar et al. |
| 6,397,105 B1 | 5/2002 | Bouhour et al. |
| 6,434,424 B1 | 8/2002 | Igel et al. |
| 6,477,416 B1 | 11/2002 | Florio et al. |
| 6,609,028 B2 | 8/2003 | Struble |
| 6,654,637 B2 | 11/2003 | Rouw et al. |
| 6,697,673 B1 | 2/2004 | Lu |
| 6,731,980 B1 | 5/2004 | Mouchawar et al. |
| 6,772,005 B2 | 8/2004 | Casavant et al. |
| 6,792,307 B1 | 9/2004 | Levine et al. |
| 6,873,875 B1 | 3/2005 | Gilkerson et al. |
| 6,904,315 B2 | 6/2005 | Panken et al. |
| 6,925,326 B1 | 8/2005 | Levine et al. |
| 6,978,175 B1 | 12/2005 | Florio et al. |
| 7,027,868 B2 | 4/2006 | Rueter et al. |
| 7,123,960 B2 | 10/2006 | Ding et al. |
| 7,130,683 B2 | 10/2006 | Casavant et al. |
| 7,218,965 B2 | 5/2007 | Casavant et al. |
| 7,245,966 B2 | 7/2007 | Betzold et al. |
| 7,248,924 B2 | 7/2007 | Casavant |
| 7,254,441 B2 | 8/2007 | Stroebel |
| 7,283,872 B2 | 10/2007 | Boute et al. |
| 2002/0038482 A1 | 4/2002 | Mennicke et al. |
| 2002/0041700 A1 | 4/2002 | Therbaud |
| 2002/0082646 A1 | 6/2002 | Casavant et al. |
| 2002/0128687 A1 | 9/2002 | Baker et al. |
| 2002/0138417 A1 | 9/2002 | Lawrence |
| 2003/0078627 A1 | 4/2003 | Casavant et al. |
| 2004/0010292 A1 | 1/2004 | Amblard et al. |
| 2004/0024694 A1 | 2/2004 | Lawrence et al. |
| 2004/0078321 A1 | 4/2004 | Lawrence |
| 2004/0117316 A1 | 6/2004 | Gillum |
| 2004/0260349 A1* | 12/2004 | Stroebel .................. 607/9 |
| 2005/0038482 A1 | 2/2005 | Yonce et al. |
| 2005/0055059 A1* | 3/2005 | Betzold et al. ............. 607/9 |
| 2005/0096708 A1 | 5/2005 | Seim et al. |
| 2005/0177197 A1 | 8/2005 | Betzold |
| 2005/0267539 A1 | 12/2005 | Betzold et al. |
| 2005/0273430 A1 | 12/2005 | Pliha |
| 2007/0203523 A1 | 8/2007 | Betzold |
| 2007/0213777 A1 | 9/2007 | Betzold et al. |

FOREIGN PATENT DOCUMENTS

| | | |
|---|---|---|
| EP | 0448193 | 9/1991 |
| EP | 0624386 | 11/1994 |
| EP | 0830877 | 3/1998 |
| EP | 1449562 | 8/2004 |
| WO | WO 95/32758 | 12/1995 |
| WO | WO 02/51499 | 7/2002 |
| WO | WO 2005/097259 | 10/2005 |
| WO | WO 2005/113065 | 12/2005 |
| WO | WO 2006/079037 | 7/2006 |
| WO | WO 2006/079066 | 7/2006 |

* cited by examiner

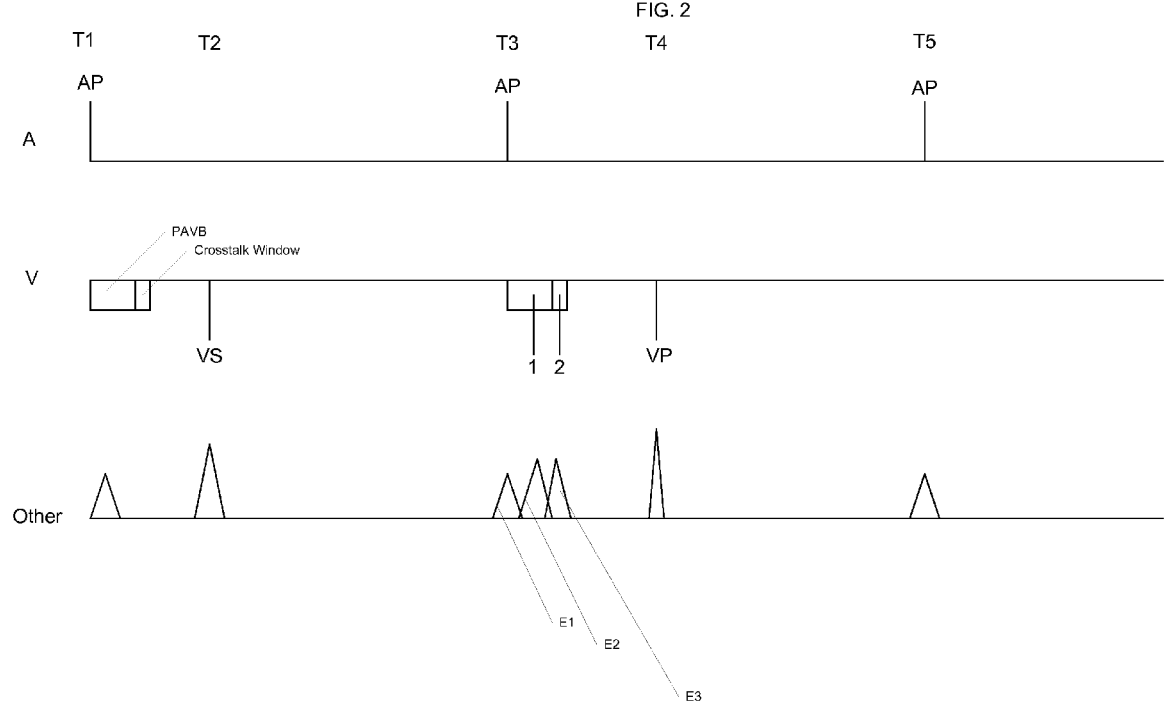

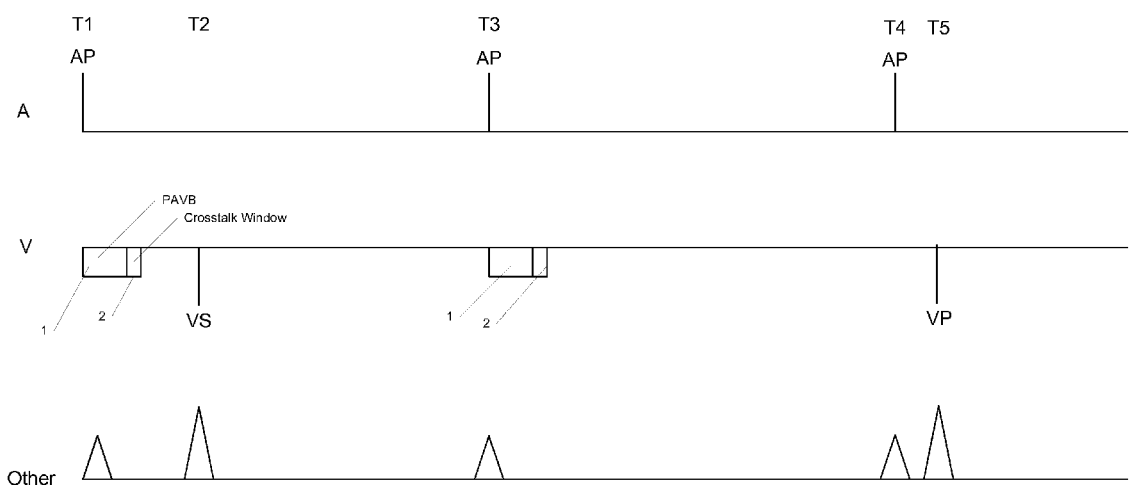

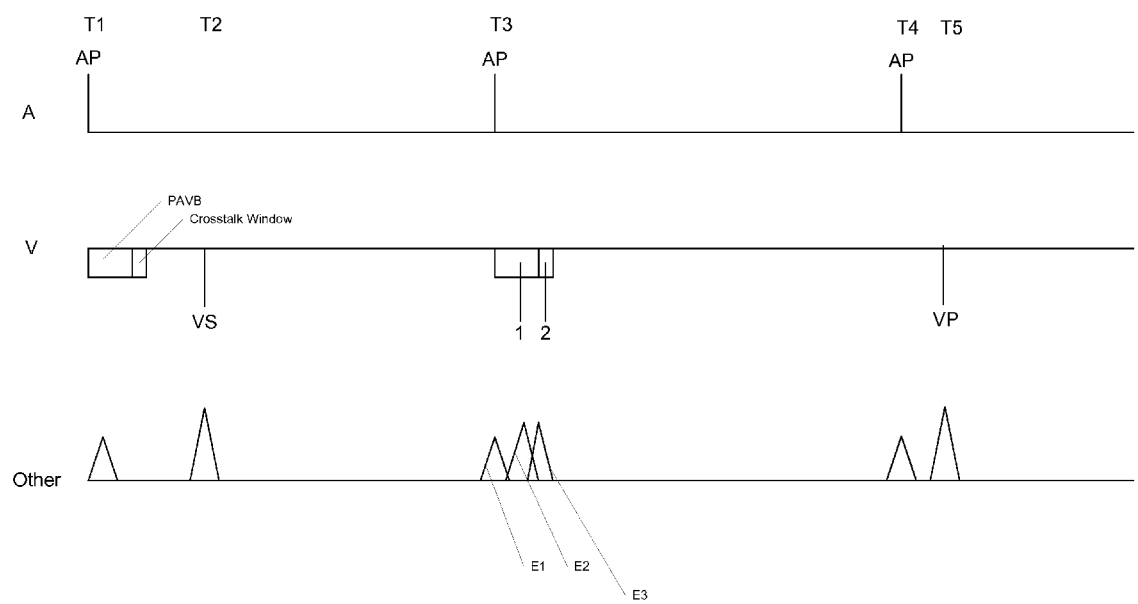

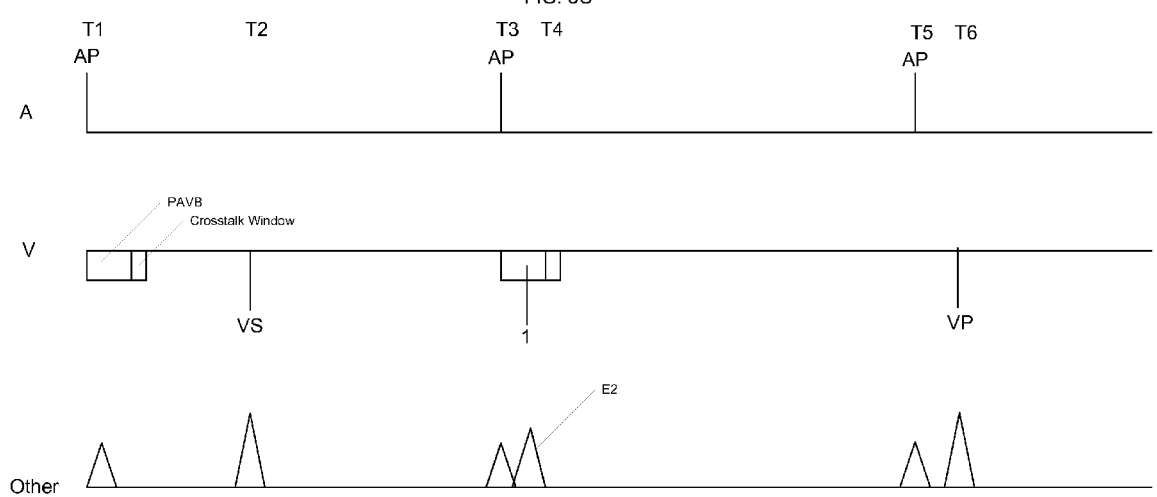

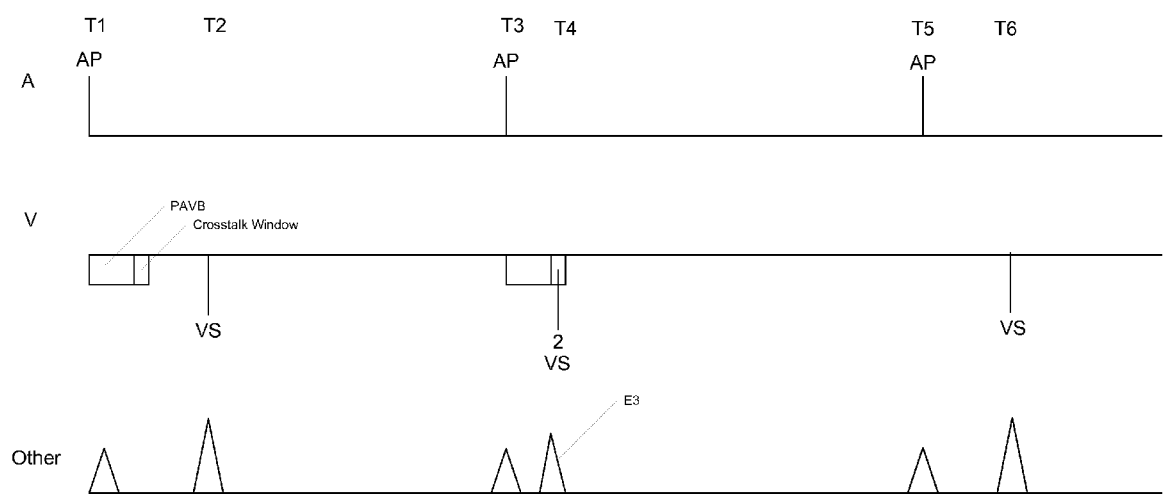

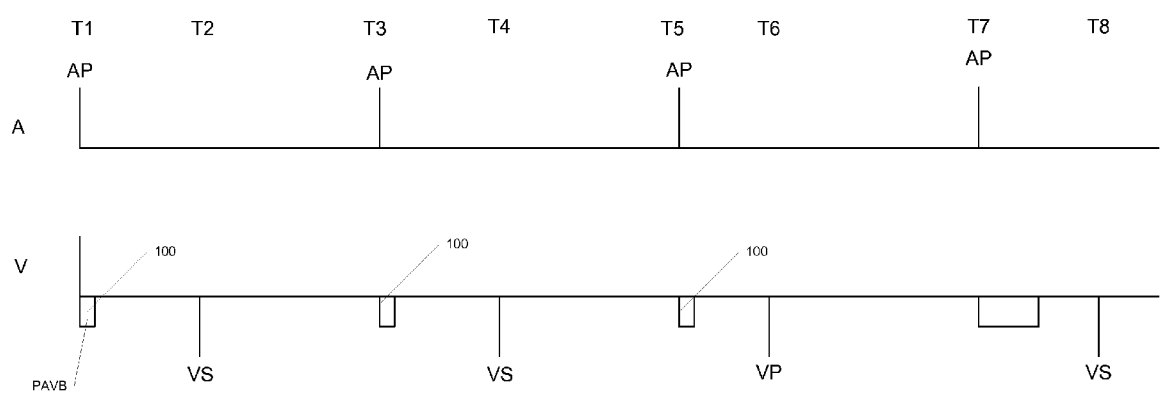

US 7,502,646 B2

PACING MODE EVENT CLASSIFICATION WITH RATE SMOOTHING AND INCREASED VENTRICULAR SENSING

FIELD OF THE INVENTION

The present invention relates to medical devices and more specifically to implantable medical devices.

DESCRIPTION OF THE RELATED ART

There are a variety of medical devices that sense data, provide diagnostic information, and/or deliver therapy. When such a device is implantable (in whole or in part), it is referred to as an implantable medical device (IMD). In the present application, IMD refers to a device that senses cardiac events and delivers pacing therapy. Such devices may or may not also include other functions such as defibrillation therapy (e.g., implantable cardioverter defibrillator (ICD)), other monitoring capabilities, alternate cardiac therapies, or non-cardiac monitoring and/or therapies. Thus, the term pacemaker may be used interchangeably with IMD in the present context with the understanding that either term may refer to a device with capabilities beyond those required of a pacemaker alone.

Recently, there has been a recognition that intrinsic conduction and ventricular depolarization, even if somewhat prolonged, is preferable to ventricular pacing; particularly pacing in or near the right ventricular apex. In general, this preference results from the unnatural propagation of a depolarization wavefront that is generated from such a pacing pulse (as compared to intrinsic depolarization).

Previous pacing modes tend to operate at one extreme or another. For example, in a true, single chamber AAI/R device, atrial pacing and sensing is possible, but no ability to provide ventricular pacing (or sensing) exists. On the other hand, DDD/R has historically been the default selection for dual chamber devices. The DDD/R mode will operate to maintain AV synchrony; however, the AV delay is necessarily such that intrinsic conduction is precluded in most cardiac cycles. This results in ventricular pacing in a very high percentage of cardiac cycles.

The present assignee has developed new modes that promote intrinsic conduction and are referred to herein generally as ventricular pacing protocols (VPP). One such VPP is Managed Ventricular Pacing™ (or MVP™) which is commercially available. A variety of VPP embodiments have previously been described, for example, as in U.S. Pat. No. 6,772,005, issued Aug. 3, 2004, to Casavant et al. U.S. application Ser. No. 10/246,816, filed Sep. 17, 2002, U.S. application Ser. No. 10/755,454, filed Jan. 12, 2004, U.S. application Ser. No. 10/850,666, filed May 21, 2004, U.S. application Ser. No. 11/115,605, filed Apr. 27, 2005, U.S. application Ser. No. 11/096,436, filed Mar. 31, 2005, U.S. application Ser. No. 10/814,692, filed Mar. 31, 2004, U.S. application Ser. No. 11/364,290, filed Feb. 28, 2006, U.S. application Ser. No. 10/971,686, filed Oct. 25, 2004, U.S. application Ser. No. 11/424,410, filed Jun. 15, 2006, U.S. application Ser. No. 11/424,383, filed Jun. 15, 2006, U.S. application Ser. No. 11/424,395, filed Jun. 15, 2006, and U.S. application Ser. No. 11/424,405, filed Jun. 15, 2006, which are herein incorporated by reference in their entirety. Other related applications include U.S. application. Ser. No. 11/258,523, filed Oct. 25, 2005, and U.S. application Ser. No. 11/257,643, filed Oct. 25, 2005.

As a generalized explanation, a VPP operates in an atrial based pacing mode to promote intrinsic conduction. Ventricular events are sensed and as long as a ventricular event is sensed in a given cardiac cycle (e.g., an A-A interval) the device continues to operate in the atrial based pacing mode. This allows for ventricular sensing during the entire A-A interval. Conversely, if there is no ventricular event, the device provides a ventricular backup pace in the subsequent cycle, timed from the atrial event (paced or sensed) that initiates this subsequent cardiac cycle. Thus, in a VPP it is possible to have an entire cardiac cycle devoid of ventricular activity while ultimately maintaining AV synchrony. There are, of course, many variations and embodiments provided that are not described herein for the sake of brevity. It should be appreciated that operation in an atrial based pacing mode includes mode switching a device into such a mode (e.g. AAI/R, ADI/R) and into a mode that provides ventricular pacing (e.g., DDI/R, DDD/R, VVI/R, etc.) as necessary and potentially on a beat by beat basis or alternatively, operation in a complex mode that includes more comprehensive behavior (e.g., FIDDI) without necessitating mode switching to achieve the functionality described.

One benefit of a VPP is that the protocol may be initiated with patients regardless of the status of their AV conduction. Those having intact or partially intact conduction will benefit in that conduction is promoted and ventricular pacing is reduced or eliminated. For those patients with heart block, the VPP will quickly move to provide ventricular pacing and periodically check to determine if conduction has returned. Both in initially recognizing the need to pace and performing the conduction checks, the methodology employed is transparent to the patient.

As previously indicated physicians implanting a dual chamber device often utilize nominal settings and program the device to DDD/R due to its simplicity. The VPP allows for the same type of comprehensive reliability across patient profiles and without the need to program numerous parameters upon implant. The VPPs are preferable in that that they reduce or minimize ventricular pacing when intact conduction is present.

BRIEF DESCRIPTION OF THE DRAWINGS

FIGS. 2-4 are timing diagrams.

DETAILED DESCRIPTION

Figure 1:
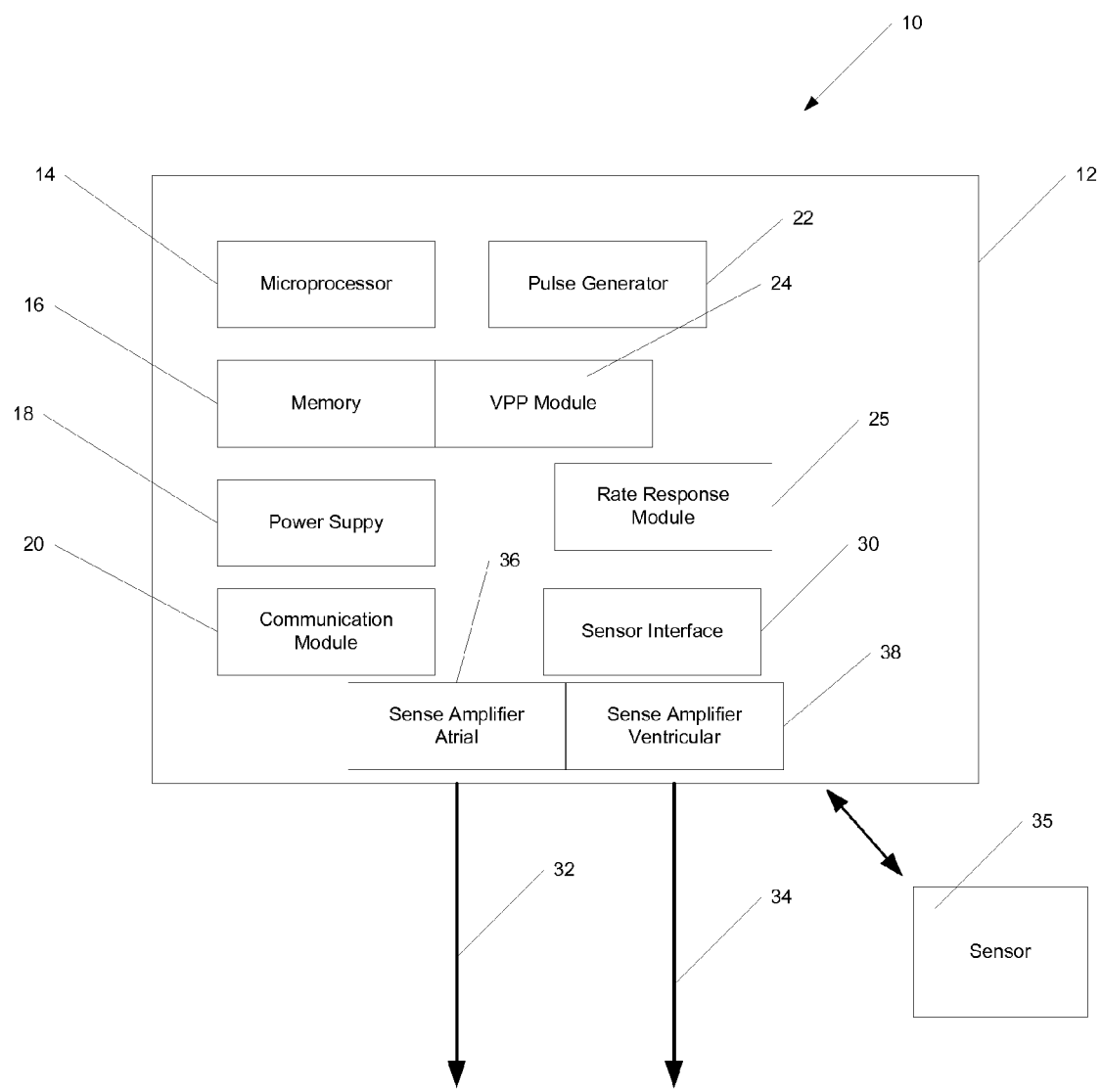
FIG. 1 is a block diagram illustrating an implantable medical device consistent with the teachings of the present invention.

FIG. 1 is a block diagram of an implantable medical device (IMD) 10 having pacing capabilities. While not illustrated, IMD 10 may also include a variety of other monitoring, diagnostic and therapeutic functions. Further, FIG. 1 is not meant to comprehensively illustrate all components of an implantable pacemaker.

The IMD 10 includes a housing 12 that contains a microprocessor 14, memory 16, a power supply (e.g., battery) 18, a communication module 20 that facilitates telemetry to an external device and a pulse generator 22 for generating pacing pulses. A rate response module 25 is provided to optionally obtain sensory input and control a pacing rate based upon perceived physiological need. A sensor interface 30 is provided to collect data from one or more sensors/electrodes, one or more of which may be disposed on leads 32, 34. The pacing stimuli generated by the pulse generator 22 are delivered via the leads 32, 34. Also illustrated in FIG. 1 is a VPP module 24. It should be appreciated that these functions may be algorithms stored in the memory 16 or incorporated into other hardware, software, or firmware.

In operation, the IMD 10 senses cardiac events and provides an appropriate response. Most typically, cardiac events are sensed via electrodes on the leads 32, 34. The input is passed through an atrial sense amplifier 36 or a ventricular sense amplifier 38, and the signal from the amplifier(s) is then processed. These processed signals are indicative of specific activities within the heart, typically represented as an electrogram (EGM) when generated from device data or an electrocardiogram (ECG) when based upon surface collected data. An alternative sensor 35 is illustrated as being in communication with the IMD 10 and may represent another implanted sensor in direct or indirect communication with the IMD or an external sensor such as ECG electrodes that may or may not be in communication with the IMD 10. As is well known, the cardiac cycle includes an atrial depolarization represented electrically by a P wave, ventricular depolarization represented by the QRS complex, and repolarization represented by a T wave. While sensing algorithms can be relatively complex, in general a sensed P wave indicates intrinsic atrial depolarization while a sensed R wave indicates intrinsic ventricular depolarization. For a given pacing mode, if a P wave or R wave is not sensed within a predetermined time frame, then the IMD 10 provides atrial or ventricular pacing with appropriate timing, if supported by that mode. There are numerous variations to this generalization such as overdrive pacing or various tachycardia pacing therapies. The main point herein is that the IMD 10 senses data and responds in some fashion to that data according to the parameters of a selected mode.

As discussed, the present invention relates to an IMD 10 that selectively operates according to a VPP, such as for example, the MVP™ mode. There are numerous variations among the VPPs and for the sake of clarity not every variation will be separately described.

FIG. 2 is a generalized timing diagram illustrating certain cardiac events as sensed on an atrial (A) channel, a ventricular (V) channel, and over an "other" channel. It should be appreciated that this diagram and those like it are not meant to accurately reflect waveforms or provide accurate temporal proportions or relationships. The "other" channel may include surface EKG, far field sensing, separate lead sensing, can electrode(s) or any sensing technique other than the lead/electrode for the particular atrial or ventricular chamber when and where a relevant event is occurring. At time T1, an atrial pace (AP) is delivered and is illustrated as a marker channel spike on the atrial channel (and could alternatively have been illustrated as a waveform). The resulting depolarization is illustrated, schematically, as a waveform on the "other" channel. Notably, no activity from the AP is present on the ventricular channel. This results from a post-atrial ventricular blanking period (PAVB). During this time, the ventricular sense amplifier 38 is disconnected (literally or effectively) from the ventricular lead 34 as the atrial pacing pulse would generate an electric field that would at the very least be sensed by the ventricular lead 34 and potentially "overwhelm" the sense amplifier 38 due to the amplitude of the signal. Absent the PAVB and other controls, two negative results could occur. The first is that the large signal produces residual effects that prevent accurate sensing with the ventricular lead, even after the atrial waveform has apparently dissipated. The second is that the atrial event is interpreted as a ventricular event on the ventricular channel. This is referred to as crosstalk. In other words, an atrial event is sensed (far field) on the ventricular lead 34 and considered as a ventricular event.

By disconnecting the sense amplifier 38 when an atrial pace is delivered, these effects are prevented from occurring. On the other hand, if a true ventricular event does occur during this time, it cannot be sensed on the ventricular channel. In addition to the PAVB, many pacing modes include a crosstalk window. This window extends beyond the PAVB; however, the sense amplifier 38 is connected. Thus, events can be sensed on the ventricular channel (including crosstalk). In general, events sensed during the crosstalk window are assumed to be crosstalk and are treated as such. The distinction is that during the PAVB ventricular sensing is precluded; during the crosstalk window sensing is permitted and the window simply defines how sensed data may be classified. It should be appreciated that these events are not drawn to scale nor are they proportionally accurate. In a typical device, the PAVB may be on the order of 30 ms and a crosstalk window may be on the order of 50-100 ms. Thus, a total interval would be 80 to 130 ms with the PAVB representing less that half of this duration. Thus, the proportions shown are provided for ease of illustration and to facilitate description and do not represent accurate temporal proportions.

Following the expiration of the crosstalk window, events sensed on the ventricular channel are generally classified as conducted events or other true ventricular events. Such an event is illustrated as a ventricular sensed event (VS) at time T2. At time T3, another AP is delivered and the PAVB (1) and crosstalk window (2) run. Referring to the "other" channel, three "events" are illustrated. The first event E1 is the waveform resulting from the atrial pace AP; just as it occurred at time T1. The second event E2 is a premature ventricular contraction (PVC). As this occurs during the PAVB, it will not be sensed on the ventricular channel. The third event E3 is also a PVC, but this PVC occurs during the crosstalk window 2. Thus, it will be sensed on the ventricular channel; however, according to many pacing modes, this PVC is "ignored" as crosstalk. Thus, regardless of whether either PVC E2 or E3 occurred, a ventricular pacing pulse VP is delivered at time T4 (according to the current mode selection, e.g., DDD/R). It should be appreciated that having two PVCs as illustrated is not likely and they are illustrated as such simply to show a PVC in each window. With continued operation in this mode, the next interval begins with an atrial pace AP at time T5. This might be typical operation in a mode such as DDD/R.

FIG. 3A is a timing diagram illustrating the relative timing that occurs when a VPP, such as for example, the MVP™ mode is utilized. In previous VPPs, the PAVB and crosstalk window exist, substantially as described above. As indicated, in a VPP mode, ventricular pacing is generally not available in a given cardiac cycle (A-A) interval, where a ventricular event occurred in the preceding cardiac cycle. Thus, at time T2, a VS occurs. Therefore, ventricular pacing will not be provided in the A-A interval defined by T3 and T4. As illustrated, no ventricular event is sensed in this interval. As such, a ventricular pace (VP) is delivered in the next cardiac cycle at time T5.

FIG. 3B continues with the same VPP. At time T3, an AP is delivered and just as illustrated in FIG. 2, three events are illustrated on the "other" channel. E2 and E3 are PVCs (again unlikely to both occur; shown together for illustrative purposes). The PVC at E2 cannot be sensed on the ventricular channel, as the sense amplifier 38 has been disconnected. The PVC at E3 can be sensed; however, since it is in the crosstalk window 2, it is ignored (i.e., believed to be atrial crosstalk rather than a PVC). In either case, no ventricular event is "sensed" (more accurately, no sensed ventricular event is classified as a ventricular event) and according to the VPP a ventricular pace VP is delivered in the next cycle at time T5. While various embodiments of the VPPs exist, many include a provision that any ventricular event, including a PVC, will "count" as a ventricular event and therefore ventricular pacing will not be provided in the subsequent A-A interval. Because the PVCs occurred during the PAVB and/or the crosstalk window, what may be considered an "unnecessary" ventricular pacing pulse is delivered at T5.

A similar scenario is illustrated in FIG. 3C. Here, the PVC E2 is illustrated. Due to the nature of the PAVB, this PVC cannot be sensed and will result in the VP at time T6. As indicated, this results in action that is contrary to normal VPP operation if such an event were sensed and classified as a PVC. In this example, a ventricular event does occur very early in the A-A interval between T3 and T5; however, this event (PVC E2) is within the PAVB window and therefore could not be detected. The ventricular pace VP is delivered rather early in the A-A interval initiated by the AP at time T5. This is potentially significant, in that a relatively short V-V interval (T2–T4) occurs and is followed by a relatively long V-V interval (T4–T6) that is terminated by ventricular pace. In a minor subset of patients, there is speculation that this type of scenario could be proarrhythmic and lead to pacemaker induced tachycardia (PIT). The validity of this concept is not presently known. What further complicates the matter is that the "other" channel data is often unavailable. Thus, when reviewing collected data from patients having a ventricular arrhythmia following a VP, the presence of the PVC in the PAVB is often unknown. As such, one might correlate the normal operation of the VPP to causation of the arrhythmia, when in fact the PVC is an unrecognized intervening factor.

FIG. 3D illustrates PVC E3 occurring during the crosstalk window 2. In other embodiments, a sensed event occurring in this window is treated as crosstalk and effectively ignored. In alternate embodiments of VPPs, events occurring during the crosstalk window are not automatically dismissed. Such embodiments are described in entitled "Ventricular Event Filtering for an Implantable Medical Device", Ser. No. 10/850,666, filed May 21, 2004, which is herein incorporated by reference in its entirety. In one such embodiment, the first (or first few) occurrence(s) of an event in the crosstalk window is treated as a PVC. If the event were truly crosstalk, then it would likely be repetitive and occur in subsequent cardiac cycles. If that is the case, these repetitive events are treated as crosstalk in those subsequent occurrences. When occurring rather infrequently, they are more likely a PVC and are treated as such. Thus, as illustrated in FIG. 3D, using such an embodiment, the PVC E3 is sensed as a VS at time T6. This "qualifies" as a ventricular event and in the subsequent cycle, ventricular pacing is not provided and a conducted ventricular event VS occurs at time T6. Thus, the above referenced application addresses PVCs occurring in the crosstalk window and may be included in various embodiments of the present invention. In the alternative, if ventricular sensed events occurring during the crosstalk window are not treated as PVCs, there presence will at least be noted upon subsequent review of data if any anomalies follow a ventricular pace delivered in the subsequent cardiac cycle.

FIG. 4 is a timing diagram illustrating one aspect of the present invention. The PAVB, in these embodiments, is considerably shortened. Typically, a PAVB with traditional modes (e.g., DDD/R) is on the order of 30 ms. The truncated PAVB is significantly shorter. In one embodiment, the truncated PAVB is 8.5 ms, though this is non-limiting. The truncated PAVB need only be sufficiently long so that the ventricular sense amplifier is disconnected when the true effects of the atrial pacing pulse will occur. Thus, in an IMD 10 capable of multiple modes, two or more PAVB intervals are retained in memory and used as described herein.

Figure 5:
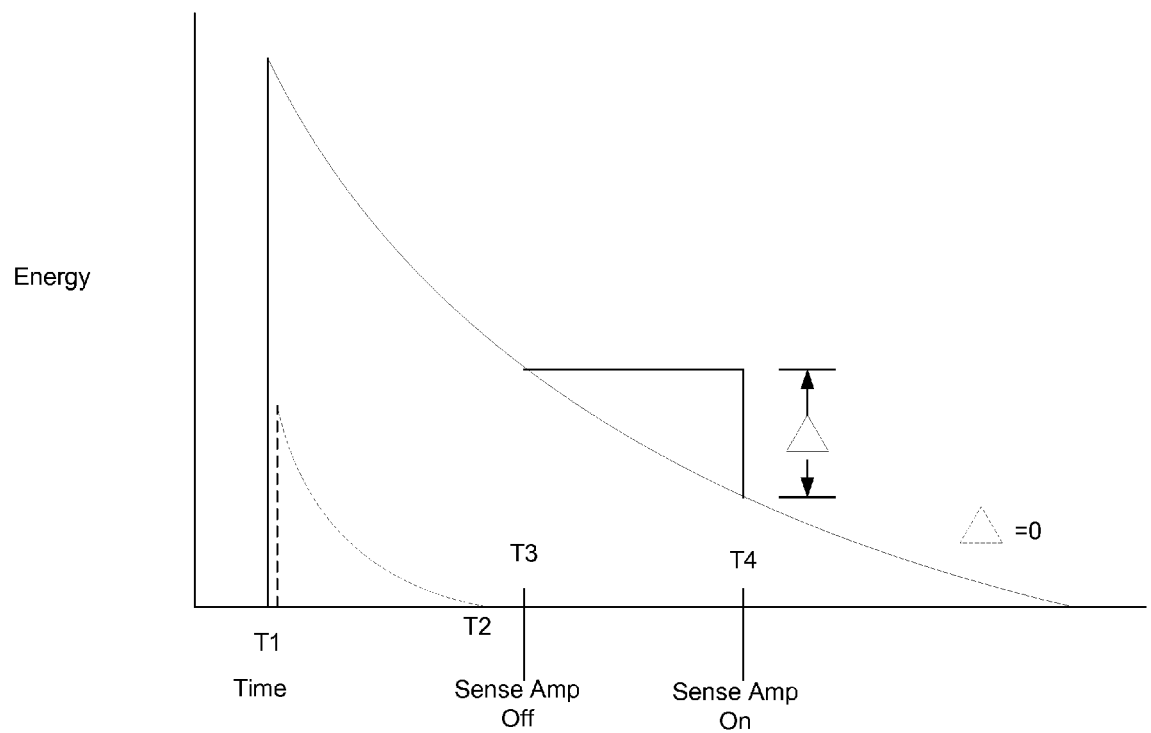
FIG. 5 is a graph illustrating ventricular pace energy dissipation.

This approach is counter to the conventional wisdom and crosstalk certainly could occur beyond the truncated PAVB. The truncated PAVB is successful when used with a VPP because the present inventors have recognized that it is ventricular pacing that typically creates crosstalk (or what has been perceived as or attributed to crosstalk) beyond the truncated window. FIG. 5 is a graph of energy versus time at an interface between an electrode and tissue. At time T1, a ventricular pacing pulse is delivered (solid line) and an intrinsic ventricular depolarization occurs (dashed line—offset for visibility); these events are not drawn to scale. The magnitude of the pacing pulse is vastly greater than the intrinsic depolarization; particularly at the tissue/electrode interface. The pacing pulse tends to create polarization about the electrode that remains for some time after the pulse. At time T3, the ventricular sense amplifier is disconnected for a PAVB and reconnected at time T4. The polarization at the interface generates a signal that is perceived by the sense amplifier 38. When disconnected, the sensed amplifier 38 "holds" at this value. Thus, when reconnected, the voltage sensed is lower than the held value (due to the decay of the polarization artifact); hence there is an energy delta between sensed values at T3 and T4. This is perceived as a ventricular event at T4 when in fact it is "crosstalk." Of course, this is not truly crosstalk (from an atrial event) in that is an artifact occurring on the ventricular lead, but is something that should be ignored just the same. FIG. 5 also illustrates that this effect does not occur from conducted events as polarization proximate the electrode is not a factor.

Returning to FIG. 4, the truncated PAVB may be used when ventricular pacing has not recently been provided. At time T5 an atrial pulse occurs and the truncated PAVB runs. At time T6 a ventricular pacing pulse VP is delivered. In the next cycle, a "normal" (i.e., long) PAVB is utilized because the polarization from the previous VP may generate errant signals.

Figure 6:
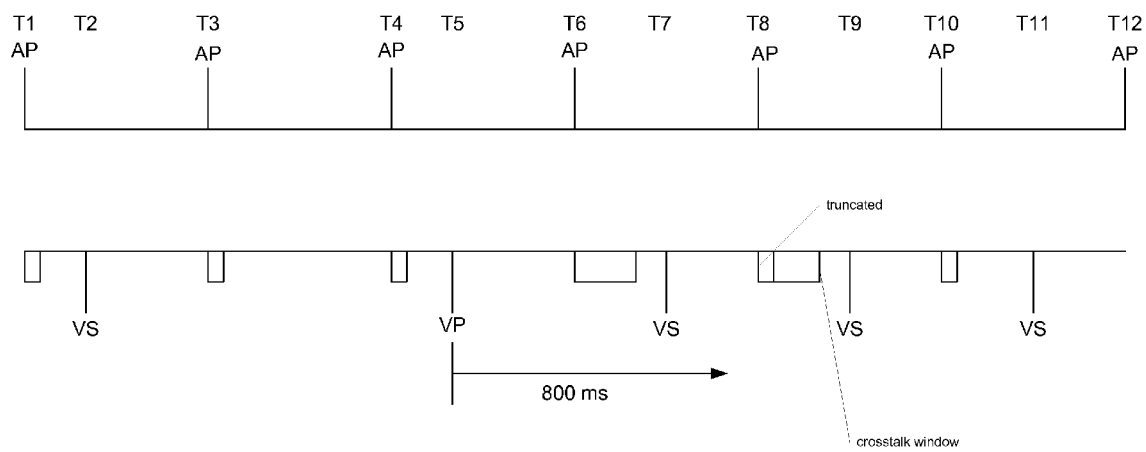
FIG. 6 is a timing diagram.

FIG. 6 illustrates use of the truncated PAVB with a VPP. At T1, an AP is delivered and a truncated PAVB is initiated. A ventricular event is sensed at T2, precluding ventricular pacing in the next cycle, which begins at T3 and has a truncated PAVB. As illustrated, no ventricular event is sensed and at T4, the next AP is delivered and another truncated PAVB begins. A ventricular backup pace VP is delivered at T5. In the next cycle, a longer PAVB is used and begins at T6. In the next three cycles illustrated, conducted ventricular events are sensed. Typically, a normal or "long" PAVB is only necessary in the cycle following the ventricular pacing pulse. The polarization effects tend to decay over a known time period. While not limiting, this has been observed to be about 800 ms. Thus, in one embodiment, the microprocessor of the IMD 10 calculates the time since delivery of a ventricular pacing pulse. Until this predetermined interval expires, any atrial event will initiate a longer PAVB. As such, at higher heart rates it is possible to have multiple cycles that utilize the longer PAVB related to a single ventricular pace. In other embodiments, the interval may be set to a value between about 400-2000 ms. Alternatively, the value may equate to a number of cardiac cycles which may be fixed or vary with heart rate.

As illustrated in FIG. 6, an 800 ms timer is initiated at time T5. As this timer does end prior to T8, the PAVB started at T8 is a truncated PAVB. The PAVB illustrated at time T8 illustrates another concept. That is, in addition to running a truncated PAVB, a crosstalk window may run and may terminate after the same duration as previously utilized. That is, the crosstalk window expired at some fixed interval following the atrial pace; with a longer PAVB, this resulted in a shorter crosstalk window. With a truncated PAVB, the crosstalk window may be lengthened so as to terminate at the same point in time relative to the atrial pace. Events are sensed during this window and may be classified as crosstalk or as a PVC depending upon the protocol parameters. The effect of the truncated PAVB, with or without a crosstalk window is that accurate ventricular sensing occurs. Thus, PVCs are not likely to be undersensed and overlooked as described in previous examples.

Figure 7:
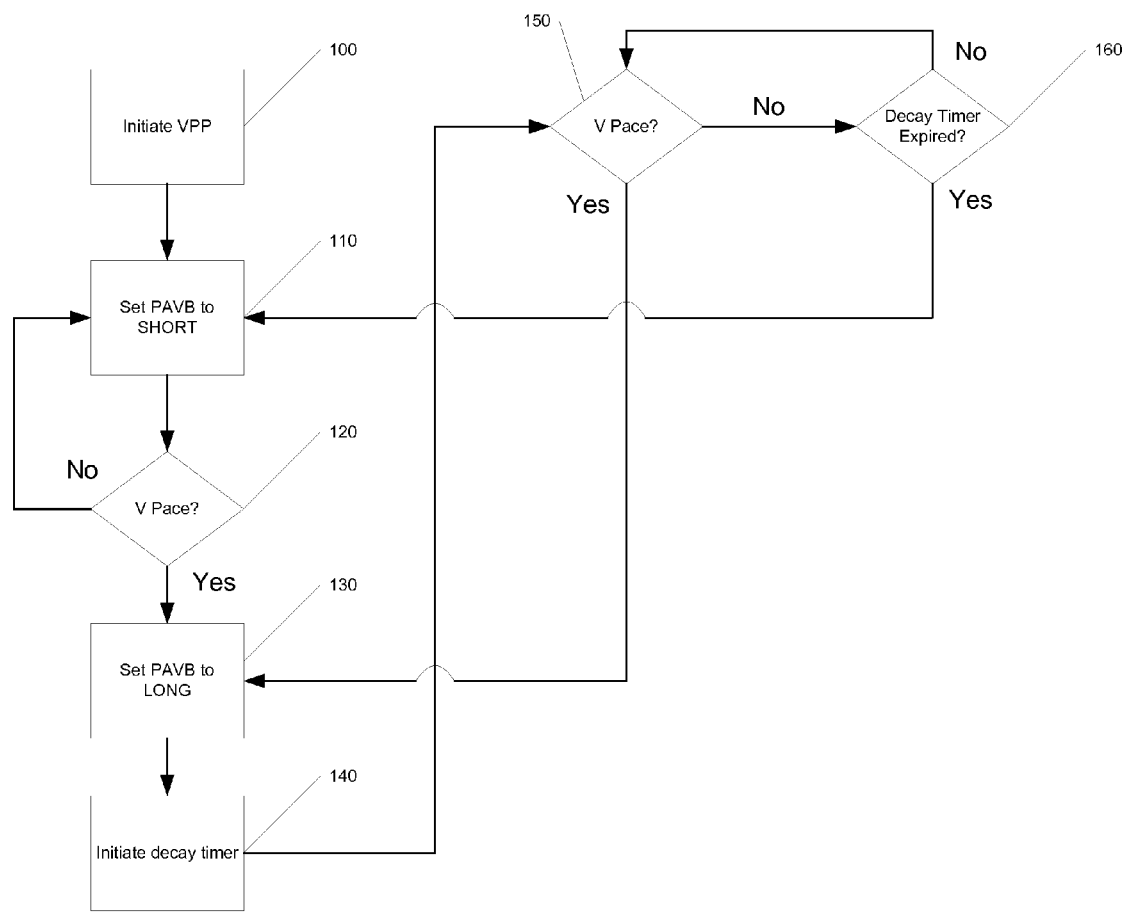
FIGS. 7-9 are flowcharts describing various processes consistent with the present invention.

FIG. 7 is a flowchart that describes the use of a truncated PAVB with a VPP. Initially, the IMD 10 begins operation (100) according to the parameters of the VPP. For illustrative purposes, we assume that there has not been ventricular pacing for some time. The PAVB is set (110) to the truncated or short value, which in one embodiment is 8.5 ms. The IMD 10 then monitors to determine if a ventricular pace (120) is delivered. Assuming there is no ventricular pacing, the PAVB is maintained at the short value (110). Thus, any event occurring after this short PAVB may be sensed on the ventricular channel. Alternatively, if a ventricular pace is (120) delivered, the PAVB interval is set to the long value or what is currently the "normal" PAVB, which may be approximately 30 ms in one embodiment. Thus, at the next atrial event, the PAVB will be at the longer value.

A decay timer is initiated (140) to determine when to revert to the short PAVB. As indicated, this may be a specific time interval (e.g., 800 ms) or may a particular number of cardiac cycles (e.g., 1, 2, 3, 4). Alternatively, polarization at the ventricular lead may be measured and/or a patient specific decay timer may be set accordingly. Subsequently, the IMD 10 continues to monitor for ventricular pacing (150). If ventricular pacing (150) occurs while the decay timer is running (or prior to the lapse of the predetermined number of cardiac cycles), the PAVB is reset to the long value (130) and the decay timer is reset (140). If no ventricular pace is delivered (150), the IMD 10 continues to monitor until the decay timer expires (160). Upon expiration, the PAVB is reset to the short value (110) and the process repeats.

In this manner, true ventricular blanking only occurs for a relatively short time period following atrial events, thus providing an increased ability to sense events, including PVCs on the ventricular channel. When ventricular pacing is provided, this PAVB is lengthened to avoid potential effects generated by polarization.

Figure 8:
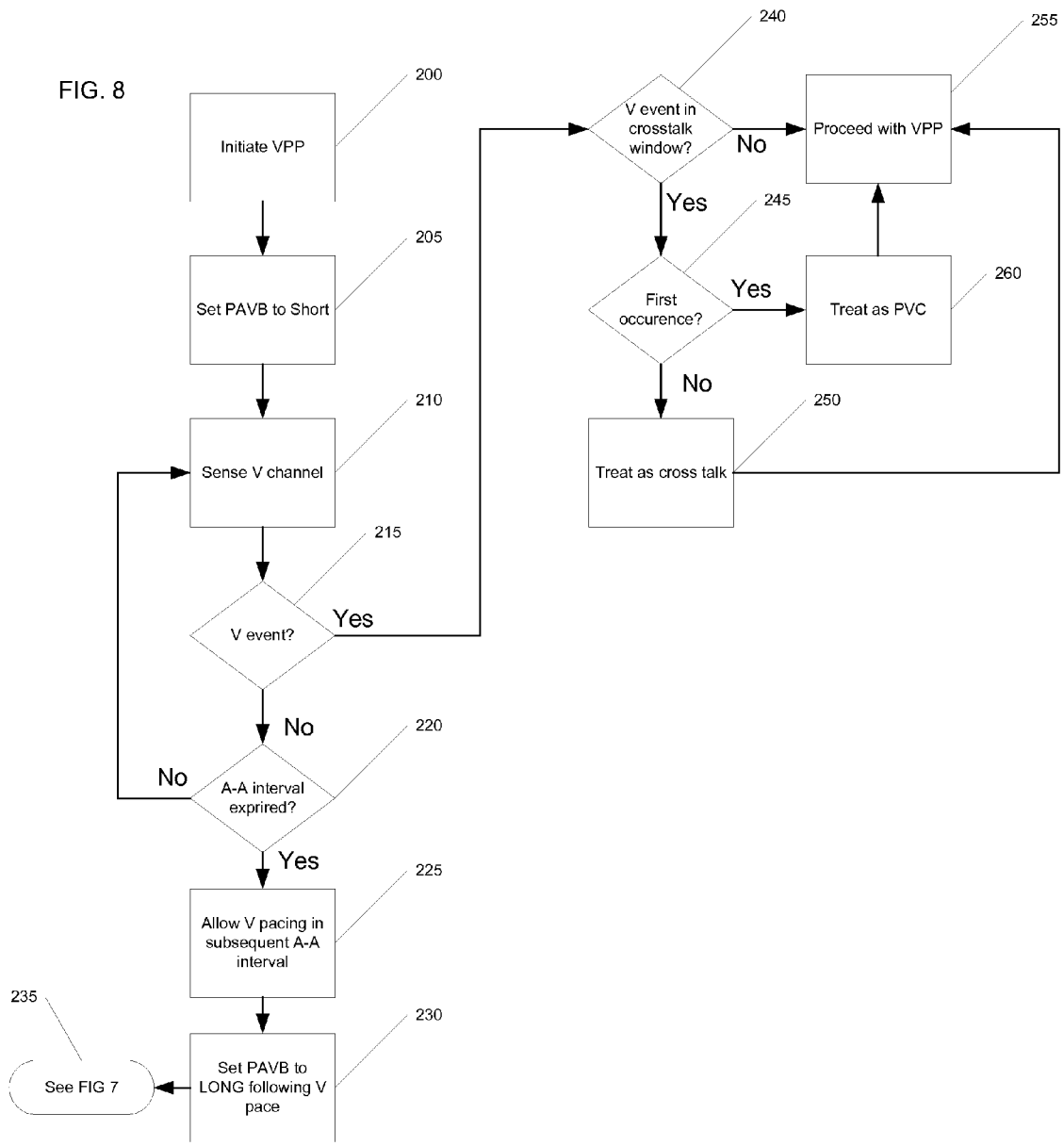

FIG. 8 is a flowchart illustrating VPP operation with a short PAVB and a crosstalk window event classification. The IMD 10 begins (200) operation in the VPP and the PAVB is set to the short interval (205). Events are sensed (210) on the ventricular channel. If no event is sensed 215, the IMD 10 determines if the A-A interval has expired (220), if not, the IMD 10 continues to monitor the ventricular channel (210). If the A-A interval has expired (220), then ventricular pacing will be permitted in the next A-A interval (which at this point in time is now the current A-A interval); in other words, ventricular pacing is permitted in an A-A interval following an A-A interval devoid of ventricular events. Assuming the ventricular pace is delivered, the PAVB is set to the long value and the process (235) follows that described in FIG. 7 beginning with step 140. If the ventricular pace is inhibited, then the process moves from step 225 to step 215 with a sensed ventricular event.

If a ventricular event is sensed at step 215, the process moves to step 240. It should be appreciated the process may move to step 240 following any sensed ventricular event whether the PAVB is set to short or long. In either case, the IMD 10 determines if the sensed ventricular event occurred (240) during the programmed crosstalk window. If not, normal operation according to the VPP occurs (255). If the ventricular event did occur during the crosstalk window (240), the IMD 10 determines if this is the first such occurrence (245). If yes, then this event (occurring during the crosstalk window) is treated as a PVC (260) and the VPP proceeds accordingly (255). In one such embodiment, the VPP considers the PVC as a ventricular event that precludes ventricular pacing in the next cardiac cycle. If not the first occurrence (245), the ventricular sense is classified as "crosstalk" (not a ventricular event) and the VPP proceeds accordingly (255). It should be appreciated that the determination of whether this is a first occurrence (245) is relative. As explained, true crosstalk is usually repetitive; thus each consecutive cycle will have the same type of event. Thus, the first occurrence is after some predetermined number of cycles devoid of similarly timed events. Furthermore, some embodiments may require more than 2 consecutive events to occur before classifying them as crosstalk. In such a case, the first, second, and third such events, for example, may be classified as PVC's (245, 260).

As previously indicated, certain events or patterns might be proarrhythmic in certain patients and the following operation is provided to determine or at least correlate or suggest what may be a pacemaker induced tachycardia (PIT) with VPP operation, where appropriate. If arrhythmia (ventricular tachycardia in this example, thus VT) occurs, the events preceding the VT are analyzed. There are several possible scenarios. In the first scenario, no ventricular pacing was provided in the cycle immediately prior to (or alternatively, in a time frame where such pacing is established to be relevant to) the earliest onset of the VT. In this case, the VT is not PIT and no correlation is drawn with the VPP.

In the second scenario, a ventricular pace was delivered in the cardiac cycle immediately preceding the onset of the VT. In addition, a PVC or consecutive PVCs occurred, where either the PVC or if consecutive, first PVC was not treated as a sensed ventricular event in the cycle before the ventricular pace. If there is a correlation to be drawn with the VPP, this is the most likely scenario. As explained above, this sequencing results in a short V-V interval, followed by a long V-V interval that is terminated with a ventricular pace. With the various options provided herein (shortened PAVB, feed forward classification, rate smoothing, etc.), the likelihood of blanking a PVC is reduced and a sensed PVC would be treated as a sensed ventricular event and therefore not result in a ventricular pace in the next cycle and/or avoid the short/long patterning. However, some embodiments would not "count" a sensed PVC and in those cases, this pattern could be associated with a PIT. As the likelihood of these events actually being related is rare, it is also quite likely just coincidental. Thus, in one embodiment, this pattern must repeat a predetermined number of times before declaring a PIT and taking an action such as disabling the VPP (e.g., switching to DDD/R). This assumes that the patient has an ICD; if the patient only has a pacemaker (IPG), then one instance may be sufficient to disable the VPP as there is generally no therapy provided to address the VT, regardless of its cause. These options regarding the number of occurrences before altering the VPP are ultimately left to the programming physician to determine the best therapeutic options for the patient.

In the context of the present invention, the most likely scenario that might be VPP associated PIT is therefore the least likely to occur when the various aspects of the invention are utilized together in various combinations. That is, PVCs are more likely to be sensed with the present invention and when PVCs are sensed they are treated as ventricular events for purposes of precluding ventricular pacing in the next cycle. Alternatively, or in addition, rate smoothing can be utilized to avoid the short/long patterning described. Of course, as these features are programmable if this VPP associated PIT pattern occurs and, for example, shortened PAVBs were disabled, then the occurrence of this event may be a trigger to enable such a feature either under physician control or automatically.

In the third scenario, a ventricular pace also immediately precedes the onset of the VT; however, there is no sensed PVC that occurs in the cycle before the ventricular pace. This is the most difficult scenario to assess. In one case, there simply is no PVC that occurred in the relevant cardiac cycle. The most likely example is a single, non-conducted atrial event outside of the refractory period, followed by a ventricular backup pace in the subsequent cycle. This pattern is permitted under the VPP. There is a remote and speculative chance that even in the absence of a PVC, a long pause due to the above described non-conducted atrial event without ventricular activity followed by a cycle with a short AV interval terminated with a ventricular pace may be related to PIT in isolated patient cases. Because the present data does not support a probability of correlation, a single occurrence should preferably be weighted away from determining that a PIT occurred as this is more likely purely coincidental; however, this may optionally lead to suspension or disablement of the VPP (indicated as a dashed line in FIG. 9). Again, if the patient does not have an ICD, any VT should be taken seriously and addressed accordingly.

In a fourth scenario, there is also a ventricular pace immediately preceding the onset of the VT and a PVC did occur; however, it was not sensed by the IMD 10. This would be referred to a true undersensing of a PVC, related most likely, to a hardware, software, or device issue. For example, a problem may develop with the IMD 10, the lead 34, a sensing electrode, or some other component(s), that results in undersensing of the PVC. This would most likely result in undersensing of all ventricular activity and would be addressed accordingly; however, this could effectively appear as the second scenario, under the right conditions. It should be appreciated that this fourth scenario is not rooted in any issued with the VPP, and would affect the IMD 10 regardless of the mode.

The IMD 10 will take certain actions if the fourth scenario occurs. If available, alternative sensor data is evaluated to try to determine if a PVC occurred that was not sensed on the primary sensing mechanism, e.g., on the ventricular lead. If a PVC is found in this manner, this moves the event to the second scenario. Assuming no PVC is identified (or no such alternative sensing exists), then the IMD 10 determines that the VT was preceded by a VP that was not preceded (in relevant time) by a PVC and/or there is a recognition of an undersensing problem. The action taken, if any will be programmed by the physician and any issue leading to undersensing, once identified, would be addressed in the known manner.

Figure 9:
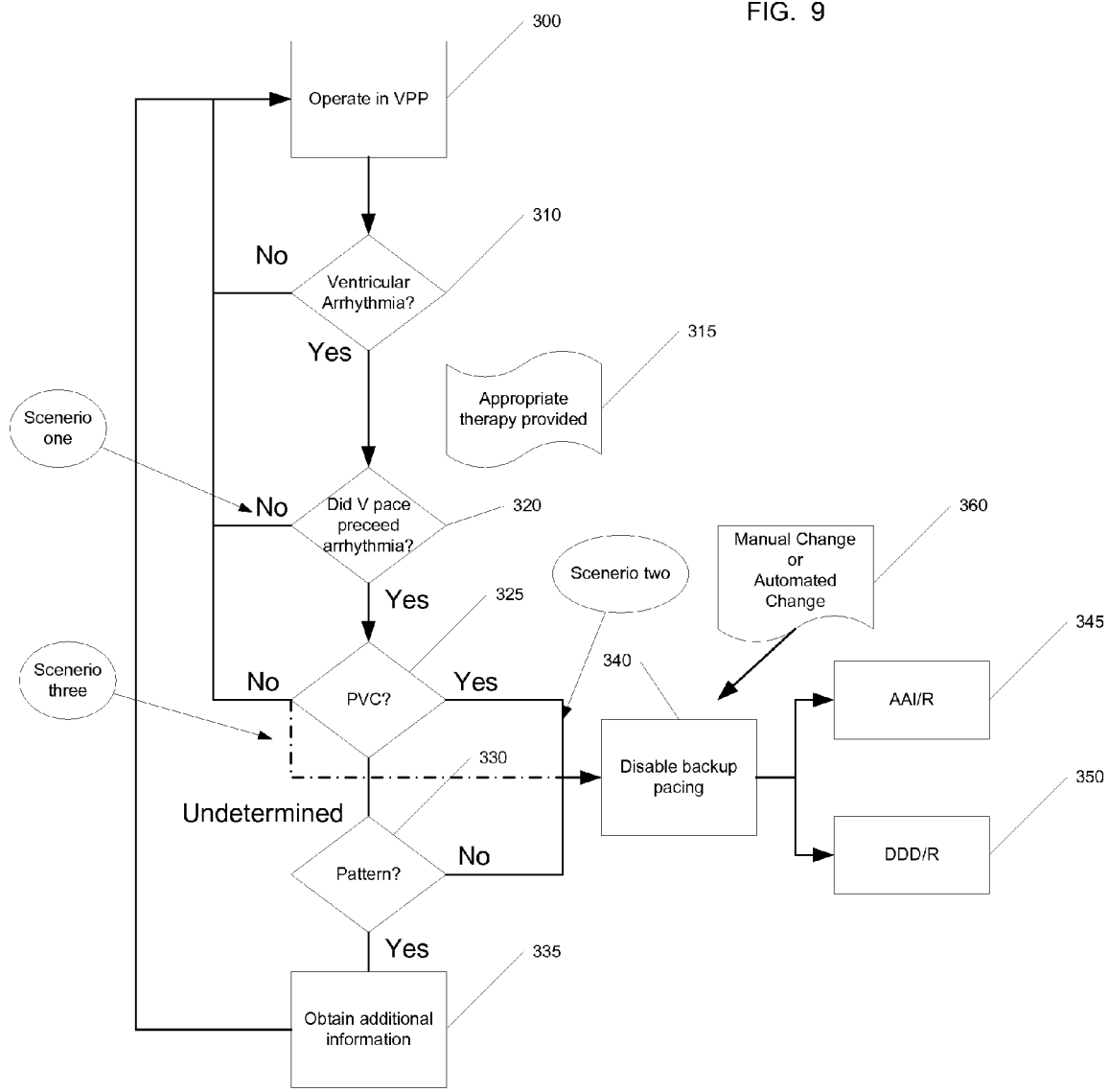

FIG. 9 is a flowchart illustrating a process for selectively altering or disabling a VPP in certain circumstances, in accordance with the above described three scenarios. Once again, the IMD 10 is initially operating according to a selected VPP (300). This may include but does not require setting a PAVB length based upon ventricular pacing and/or classifying events in a crosstalk window. As operation continues in the VPP, the IMD 10 monitors (310) for ventricular arrhythmias, particularly ventricular tachycardia or ventricular fibrillation (a similar process may be employed as described for atrial arrhythmias). If such an arrhythmia occurs, the IMD 10 provides (315) the appropriate therapy which may include operation in a mode other than the VPP for some period of time. The present methodology assumes successful termination of the ventricular arrhythmia and the ability to return to operation in the VPP. If the IMD 10 does not have a therapy option for the ventricular arrhythmia, the process presumes that the ventricular arrhythmia self terminates or is addressed by another medical treatment. A determination is made as to whether a ventricular pace (delivered according to the VPP) preceded (320) the initiation of the ventricular arrhythmia. This may include immediately preceding the event or up to a set number of cardiac cycles (e.g., 1, 2, 3, 4 or more) where the events are likely to be related. In one embodiment, the ventricular pace must occur in the cardiac cycle immediately prior to the onset of the arrhythmia to be relevant to the current decision process. The longer the time period between a ventricular pace and a ventricular arrhythmia, the less likely they are related; however, the time frame may be programmed in some embodiments.

If the ventricular arrhythmia was not preceded by a ventricular pace (320) in the relevant time period, then operation of the VPP is not likely a cause or a factor related to that event. Thus, operation in the VPP is permitted (300). This is scenario one, as described above.

It should be appreciated that one or more particularly long pauses, terminated by an intrinsic ventricular depolarization might by pro-arrhythmic in a very small subset of patients having long QT intervals. Thus, while not separately illustrated, ventricular arrhythmia proceeded by relatively long pauses where the patient is known to have or is sensed to have long QT intervals may be treated in a manner similar to that described below for instances where a ventricular pace does precede arrhythmia, even though no ventricular pace occurs. In other words, if long pauses and long QT intervals are demonstrably related to ventricular arrhythmia, then various options are available such as rate smoothing (as described herein) or switching to a non-VPP mode to avoid these pauses.

Returning to FIG. 9, if a ventricular pace did precede the onset of ventricular arrhythmia (320), then the IMD 10 determines if there was a PVC prior to the ventricular pace. In one embodiment, the ventricular pace must occur immediately prior to the onset of the ventricular arrhythmia and the PVC must occur in the cardiac cycle immediately prior to that cycle when the VP was delivered. If a PVC occurred (325), then it is possible that this event and the ventricular pace could lead to PIT and as such, the VPP may be disabled (340). This is scenario two, as described above. This may include operation in true AAI/R (345), VVI/R, a combined AAI/R VVI/R mode where the ventricular rate is very low (e.g., 30-40 bpm), or DDD/R (350). In other words, operation in the VPP is terminated or suspended temporarily or permanently; this includes suspending periodic conduction checks that would normally occur in, e.g., DDD/R. This change may occur automatically or may be made manually by a caregiver programming the IMD 10 based upon data collected by the device. In general, a change out of the VPP is less desirable, but if it must be made changing to a comprehensive mode such as DDD/R is preferred. AAI/R would not provide ventricular pacing even if required, VVI/R does not provide atrial pacing, and the combined AAI/R VVI/R does not maintain AV synchrony.

As indicated, the vast majority of patients not only tolerates but benefit greatly from utilization of the VPP. It is not believed likely that this algorithm is likely to facilitate ventricular arrhythmia. Thus, because of the low likelihood of correlation, more than one such event may be required prior to disabling backup pacing (340) (i.e., VPP). That is, two or more occurrences of ventricular arrhythmia proceeded by ventricular pacing (within a VPP) with a PVC and without other discernable causes may be required before disabling the VPP, in one embodiment. Again, this assumes that the patient has an ICD. If the patient has only a pacemaker, one such occurrence may be sufficient to disable the VPP (340) out of an abundance of caution, even though a correlation to the VPP remains unlikely. Ultimately, these are programmable features selectable by the caregiver.

Returning to step 325, the IMD 10 may not be able to determine if a sensed signal is a PVC. Thus, the relevant cardiac cycles are evaluated to determine if there is a discernable pattern that would cause the undetermined event. If such a pattern exists, then the sensed data is likely crosstalk and not a PVC; thus, the process proceeds to step 335. If no such pattern exists, then the event may be classified as a PVC and if appropriate, the process proceeds to step 340. Whether there is or is not a pattern, additional information may be obtained (335) while operation in the VPP continues. The additional information may be monitoring subsequent cardiac cycles to identify a pattern, if present. That is, due to the low likelihood of an association between operation in the VPP and PIT, questionable events may be further evaluated for a period of time before taking an action.

In an alternative embodiment, additional steps are taken to identify whether or not a PVC is present (325) in a relevant cardiac cycle. As explained, the PAVB may be truncated to allow direct sensing on the ventricular channel for a greater period of time. Even so, there is still a brief period of time where such sensing is disabled. Furthermore, it is possible that a "long" PAVB is running due to an earlier ventricular pacing pulse. This would be most likely to occur at a higher pacing rate. Of course, a given embodiment may not have the short PAVB capability or have that capability programmed off (in other words, a clinician may choose to disable the short PAVB functionality). Finally, for any number of possible reasons a PVC may occur that is simply not sensed by the ventricular lead whether due to a problem with that lead; an anomalous condition; extraneous noise; or some other factor.

When appropriate, a concerted effort may be made to identify such an event, beyond relying upon direct sensing on the most likely lead/electrode (e.g., ventricular pace/sense electrode). Thus, alternative sensor 35 and/or atrial lead 32 may be utilized to attempt to identify the presence of a PVC (or any undersensed ventricular event). This action may be taken in every cycle; taken in every cycle but only after an initial suspect arrhythmia has occurred; or the data may be stored (and not immediately processed) and only processed when there is a lack of ventricular activity indicated by the primary sensing lead (ventricular lead 34 in this example).

The atrial lead 32 may be used to detect the ventricular events via far field sensing. The alternative sensor 35 may include other lead/electrode combinations (e.g., a can electrode) or other sensing devices that are either implanted or external. For example, in a suspect patient a Holter monitor or implantable loop recorder may be provided to sense and collect such data either for subsequent review or may be in communication with the IMD 10. In summary, multiple sensing techniques are available to determine whether or not a PVC occurred (325).

FIG. 9 primarily addresses scenarios one and two as previously described. It should be appreciated that the third scenario (dashed line) would be similarly illustrated and rather than resuming normal VPP operation if no PVC is detected, the VPP may be disabled (340) after a "yes" in step 320. Again, there is a greater chance that such events are coincidental rather than related; however, the option to disable or suspend the VPP is provided. Should more than one such event sequence occur, the probability of correlation increases.

It should be appreciated that other relevant events may have lead to or contributed to the ventricular arrhythmia. Some of these events may be sensed by the IMD while many may not. Thus, in some embodiments, any decision to terminate or suspend operation of the VPP is made manually by a clinician. For example, a recent medication adjustment or missed dose, particularly strenuous exercise, high stress levels, other illnesses or a plethora of other factors may have caused or contributed to the arrhythmia. The clinician may be able to identify these factors when consulting with the patient whereas the IMD would not have the ability to obtain such information. As such, ventricular pacing may be coincidental with the arrhythmia and not a cause.

As described in more detail in commonly assigned, previously referenced copending applications P25415.00, P26089.00, P26091.00 and P23959.00, which are herein incorporated by reference in their entireties, various smoothing functions are provided in combination with VPP operation. The smoothing function may be specifically utilized in the event of a PVC or may be utilized when patient specific information indicates that a ventricular sense is unlikely in a given cardiac cycle. While reference should be made to the incorporated documents, a summary is provided herein for illustrative purpose and should not in any way be interpreted to limit the copending applications.

VPP smoothing, as indicated, has two generalized variations. The first is used when a PVC occurs either very early in an A-A interval or after a properly conducted ventricular event. With an early PVC, V-V intervals (including the PVC as a V event) will tend to vary, even with a fixed atrial rate. Thus, there may be a normal V-V, followed by a relatively short V-V, followed by a relatively long V-V. In some cases, the last V-V may be quite long and may be terminated by a ventricular pacing pulse. As previously described, a VPP does not control ventricular timing and only provides ventricular pacing in a cardiac cycle where the previous cardiac cycle was devoid of ventricular activity. Thus, to smooth these V-V variations, the VPP accelerates atrial timing; that is, an atrial pace is delivered early (with respect the current atrial rate). This shortens the A-A interval that includes the PVC and assuming intrinsic conduction in the next A-A interval(s), the resulting intrinsic V-V interval is "modified." The early PVC creates a relatively short V-V interval (e.g., V sense-PVC), which cannot be avoided; however, by deliberately and precisely shortening the A-A interval (which can be controlled via the VPP), the next V-V (PVC–V sense) interval will likely be shorter. This avoids the short-long pattern that is potentially disruptive. By repeating this procedure over a number of cardiac cycles, the resulting V-V interval is gradually returned to the pre-PVC duration; hence the smoothing effect.

A similar approach is taken with a PVC that occurs after a conducted ventricular event in a given A-A interval. Conventional practice was to delay the next cycle (e.g., initiate a VA interval from the PVC). With the rate smoothing VPP, the A-A interval is again controlled (and shortened) to effect a desired V-V interval and avoid large relative changes from one cycle to the next.

The second generalized VPP smoothing variation occurs without a PVC in a given cycle. Again, a VPP will not provide ventricular pacing in a cardiac cycle when a ventricular event occurred in the immediately previous cycle. This provides the greatest chance that intrinsic conduction will occur, even at relatively long P-R intervals that would not be tolerated by a mode such as DDD/R. With that said, for a given patient the AV intervals will be reasonably consistent for a given rate, even if long in comparison to other pacing mode standards. Thus, a range is established as to when a sensed ventricular event is expected to occur for a given patient. If no event is sensed during this range, an early atrial pace is scheduled. In other words, the IMD 10 determines that a ventricular event is unlikely in this cycle and seeks to initiate the next cycle as early as feasible. The reason for this action is that in the vast majority of situations where a ventricular beat is "skipped", normal conduction will return in the next cycle. Thus, this next cycle is started early. Since the truncated cycle was devoid of ventricular activity, ventricular pacing is now available; however, the PAV (paced AV interval) is set to a value as long as or longer than the expected intrinsic AV and this promotes intrinsic conduction. If conduction fails, the ventricular pace is delivered, generally no later than it would have been had the previous A-A interval not been truncated. The net result is that if ventricular pacing is required, the preceding V-V interval is no longer than it would be with other embodiments of the VPP (and would be shorter in some cases). Furthermore, this function very likely results in an intrinsic ventricular event following a skipped beat rather than requiring a ventricular pace. In addition, the timing of the V-V intervals with intrinsic conduction will vary less relative to one another, despite the skipped beat in the truncated A-A interval.

In various rate smoothing algorithms, the IMD 10 utilizes data indicative of the patient's intrinsic AV interval (AP-VS) to strategically pace the atrium to achieve the smoothing. Consideration is also given to a possible retrograde p-wave after a PVC so as to not pace the atrium while refractory since the pace will not capture the atrium.

Figure 10:
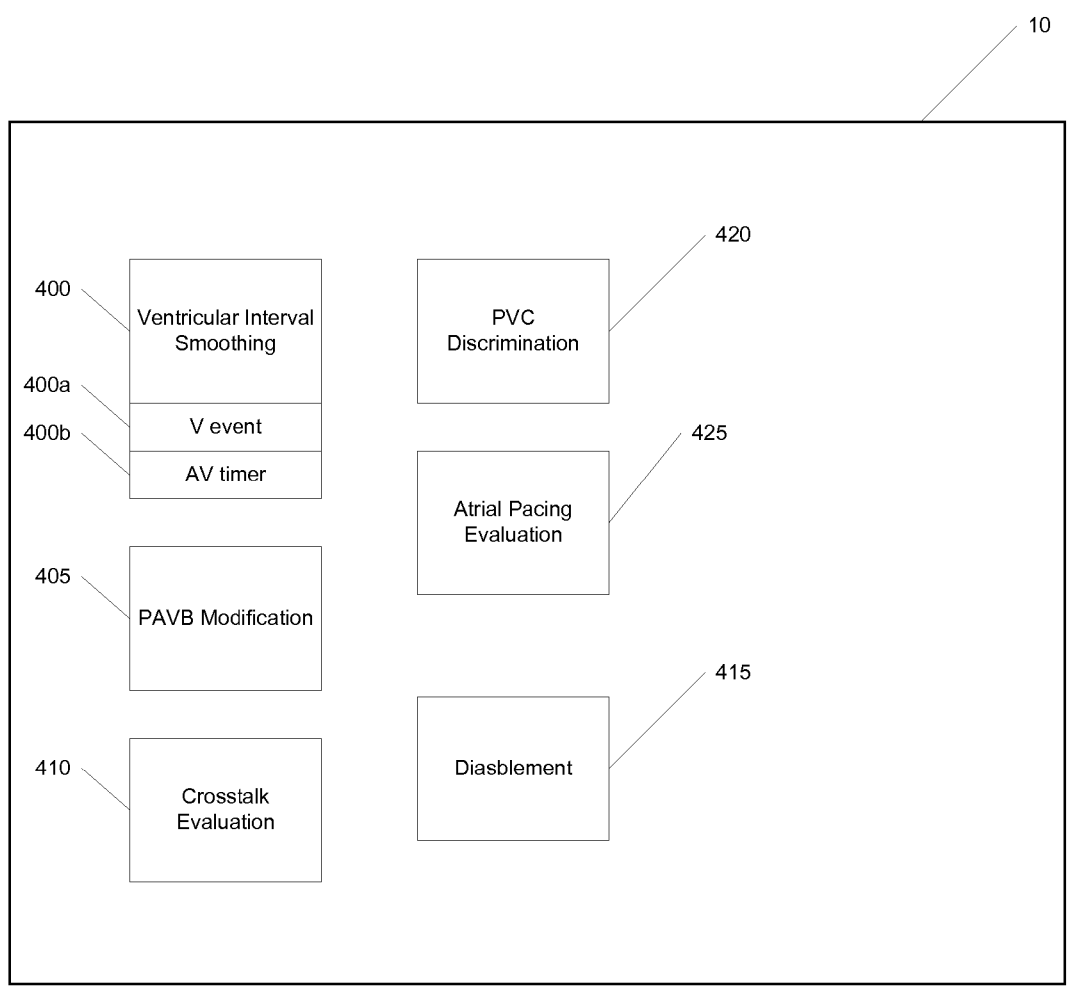
FIG. 10 is a block diagram illustrating components of an implantable medical device consistent with the teachings of the present invention.

FIG. 10 is a block diagram of the IMD 10 with a number of modules represented that provide for the various embodiments and functions described herein. The various modules may be used alone or in any combination. As illustrated, there is a VPP ventricular smoothing module 400 having a PVC module 400a and an expected AV time module 400b. A PAVB modification module 405 is provided that provides at least a long and short PAVB for use when ventricular pacing is or is not provided in a relevant time period. The crosstalk evaluation module 410 determines how ventricular sensed events occurring in the crosstalk window are handled and may classify certain events as PVCs. A disablement module 415 evaluates various events and is able to either disable (or suspend) the VPP or recommend that action. There is also a PVC discrimination module 420 that attempts to identify the presence or absence of a PVC using the various mechanisms discussed. Finally, there is an atrial pacing evaluation module 425 that evaluates the necessity of atrial pacing, as will be described herein.

One of the benefits of using a VPP is the reduction in ventricular pacing. Not only does this reduce the physiological effects created by ventricular pacing it also conserves power in the implantable device. Atrial pacing (or the resulting waveform) more closely approximates atrial depolarization. This is due to the ability to place the lead in the right atrial chamber proximate to or at least not in serious contravention with the SA node. As a result, there is generally very little hesitation in providing atrial pacing. Thus, while there is not necessarily any known negative physiological effect from atrial pacing, there may be an over reliance upon the function and possibly a tendency to over utilize the capability.

The atrial pacing evaluation module 425 works in conjunction with the VPP to potentially reduce atrial pacing, particularly rate responsive pacing. That is, the IMD 10 will periodically evaluate the necessity of atrial pacing. A rate response module takes data from one or more physiological sensors to determine a pacing rate (or pacing may be set to a particular constant rate). By withholding atrial pacing, the underlying atrial rhythm or rate will emerge. For those patients who are truly chronotopically incompetent, atrial pacing will be necessary and will be provided. However, in other patients the activity sensor indicated rate (or programmed rate, e.g., LRL) is compared with the intrinsic atrial rate. Presumably, atrial pacing would already be inhibited where the sensor rate is below the intrinsic rate; the atrial pacing evaluation module permits reliance upon the intrinsic rate even if lower than the sensor rate assuming that they are sufficiently close. The particular difference that is tolerated will be programmable by the clinician. For example, as long as the intrinsic rate is within e.g., 10% of the sensor rate, the intrinsic rate is permitted to control. In other embodiments, the difference may be 5-25%. The variations may be on a beat per minute basis and may be different at different rate levels. Of course, whenever required for any given therapy as described herein or in other known therapies (e.g., atrial overdrive pacing) the IMD 10 will provide atrial pacing as needed.

The present invention has been shown and described with respect to various embodiments. One of ordinary skill in the art will recognize that numerous variations and combinations not specifically described are within the spirit and scope of the present invention.

The invention claimed is:

1. A method comprising:
operating an implantable medical device (IMD) according to a ventricular pacing protocol (VPP) wherein a sensed ventricular event in a first cardiac cycle precludes cardiac pacing in a second cardiac cycle immediately subsequent to the first cardiac cycle;
initiating a first post atrial ventricular blanking (PAVB) interval following a first atrial pacing pulse under a first condition;
sensing an electrical signal and providing a first sensed indicator representative of cardiac activity;
accelerating the first cardiac cycle by delivering a second atrial pacing pulse to terminate the first cardiac cycle early in response to the first sensed indicator;
initiating a second PAVB following the first atrial pacing pulse under a second condition, wherein the first PAVB is shorter in duration than the second PAVB; and
providing a crosstalk window subsequent to the atrial pacing pulse during which time sensing is permitted on a ventricular channel and events sensed during the crosstalk window are evaluated according to a feed forward protocol.

2. The method of claim 1, wherein the first condition is when a ventricular pacing pulse has not been provided within a first predetermined interval prior to the atrial pacing and the second condition is when a ventricular pacing pulse has been provided within the first predetermined interval prior to the atrial pacing pulse.

3. The method of claim 2, wherein the feed forward protocol classifies a current event sensed during the crosstalk window as a PVC unless a predetermined number of immediately preceding cardiac cycles each contained a ventricular event sensed during their respective crosstalk windows in which case the current event is classified as crosstalk.

4. The method of claim 3, wherein a PVC is considered a sensed ventricular event for the VPP and precludes ventricular pacing in the next cardiac cycle.

5. The method of claim 2, wherein the first sensed indicator is a premature ventricular contraction (PVC).

6. The method of claim 2, wherein the first PAVB is about 8.5 ms and the second PAVB is about 30 ms.

7. The method of claim 2, wherein the first sensed indicator is an expiration of an AV interval timer.

8. The method of claim 7, further comprising:
initiating the second cardiac cycle with delivery of the second atrial pacing pulse so that ventricular pacing is permitted in the second cardiac cycle; and
initiating a paced AV (PAV) interval timer having a duration expected to permit intrinsic conduction to occur and to deliver a ventricular pacing pulse upon termination of the PAV if no ventricular event has been sensed prior to termination of the PAV.

9. The method of claim 5, further comprising:
modifying atrial interval timing over a plurality of cardiac cycles to return a heart rate to a pre-acceleration rate.

10. An implantable medical device (IMD) comprising:
a processor;
a pulse generator in communication with the processor for selectively providing cardiac pacing stimuli;
a lead system operably coupled to the pulse generator and the processor to deliver the cardiac pacing stimuli and to sense an electrical signal and provide a first sensed indicator representative of the cardiac data, wherein the lead system includes sensing means for sensing the electrical signal;
a ventricular pacing protocol (VPP) module operably coupled to the processor and configured to receive the first sensed indicator indicative of a sensed ventricular event in a first cardiac cycle and to preclude cardiac pacing in a second cardiac cycle immediately subsequent to the first cardiac cycle;
a pacing control module coupled with the processor and configured to initiate a first post atrial ventricular blanking period (PAVB) following an atrial pacing pulse if a first condition is met and initiate a second PAVB, longer in duration than the first PAVB, if a second condition is met and to run a crosstalk window during which sensed ventricular events are classified as a PVC unless a predetermined number of immediately preceding cardiac cycles each contained a ventricular event sensed during their respective crosstalk windows in which case the current event is classified as crosstalk; and
a VPP rate smoothing module configured to deliver a second atrial pacing pulse following the first PAVB to terminate a current cardiac cycle early in response to the first sensed indicator.

11. The IMD of claim 10, wherein the first condition is when a ventricular pacing pulse has not been provided within a first predetermined interval prior to the atrial pacing and the second condition is when a ventricular pacing pulse has been provided within the first predetermined interval prior to the atrial pacing pulse.

12. The IMD of claim 11 wherein the first sensed indicator is a premature ventricular contraction (PVC).

13. The IMD of claim 11 wherein the first sensed indicator is an expiration of an AV interval timer.

14. An apparatus comprising:
means for operating an implantable medical device (IMD) according to a ventricular pacing protocol (VPP) wherein a sensed ventricular event in a first cardiac cycle precludes cardiac pacing in a second cardiac cycle immediately subsequent to the first cardiac cycle;
means for initiating a first post atrial ventricular blanking (PAVB) interval following an atrial pacing pulse under a first condition;
means for sensing an electrical signal and providing a fist sensed indicator representative of cardiac activity;
means for initiating a second PAVB following the atrial pacing pulse under a second condition, wherein the first PAVB is shorter in duration than the second PAVB;
means for accelerating the first cardiac cycle by delivering a second atrial pacing pulse to terminate the first cardiac cycle early in response to the first sensed indicator; and
means for providing a crosstalk window subsequent to the atrial pacing pulse during which time sensing is permitted on a ventricular channel and events sensed during the crosstalk window are evaluated according to a feed forward protocol.

15. The apparatus of claim 14, wherein the first condition is when a ventricular pacing pulse has not been provided within a first predetermined interval prior to the atrial pacing and the second condition is when a ventricular pacing pulse has been provided within the first predetermined interval prior to the atrial pacing pulse.

16. The apparatus of claim 15, wherein the feed forward protocol classifies a current event sensed during the crosstalk window as a PVC unless a predetermined number of immediately preceding cardiac cycles each contained a ventricular event sensed during their respective crosstalk windows in which case the current event is classified as crosstalk.

17. The apparatus of claim 16, wherein a PVC is considered a sensed ventricular event for the VPP and precludes ventricular pacing in the next cardiac cycle.

18. The apparatus of claim 16, wherein the predetermined number of immediately preceding cardiac cycles is one.

19. The apparatus of claim 16, wherein the first PAVB is about 8.5 ms and the second PAVB is about 30 ms.

20. The apparatus of claim 15, wherein the first sensed indicator is a premature ventricular contraction (PVC).

21. The apparatus of claim 15, wherein the first sensed indicator is an expiration of an AV interval timer.

22. The apparatus of claim 15, further comprising:
means for initiating the second cardiac cycle with delivery of the second atrial pacing pulse so that ventricular pacing is permitted in the second cardiac cycle; and
means for initiating a paced AV (PAV) interval timer having a duration expected to permit intrinsic conduction to occur and to deliver a ventricular pacing pulse upon termination of the PAV if no ventricular event has been sensed prior to termination of the PAV.

* * * * *